(12) United States Patent
Lee et al.

(10) Patent No.: US 11,559,809 B2
(45) Date of Patent: Jan. 24, 2023

(54) ENHANCED CELL/BEAD ENCAPSULATION METHODS AND APPARATUSES

(71) Applicant: The Regents of the University of California, Oakland, CA (US)

(72) Inventors: Abraham P. Lee, Irvine, CA (US);
Roger Shih, Irvine, CA (US);
Wei-Feng Fang, Irvine, CA (US);
Naiqing Zhang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 424 days.

(21) Appl. No.: 16/572,293

(22) Filed: Sep. 16, 2019

(65) Prior Publication Data
US 2020/0009569 A1 Jan. 9, 2020

Related U.S. Application Data

(62) Division of application No. 15/395,744, filed on Dec. 30, 2016, now abandoned.
(Continued)

(51) Int. Cl.
*B01L 3/00* (2006.01)
*C12N 5/00* (2006.01)
(Continued)

(52) U.S. Cl.
CPC ........ *B01L 3/502784* (2013.01); *B01F 23/41* (2022.01); *B01F 31/57* (2022.01);
(Continued)

(58) Field of Classification Search
CPC ....... B01L 3/502784; B01L 2300/0867; B01L 2400/0439; B01L 2400/0487;
(Continued)

(56) References Cited

U.S. PATENT DOCUMENTS

| | | | |
|---|---|---|---|
| 2005/0032240 A1* | 2/2005 | Lee | B01J 13/02 436/180 |
| 2009/0068170 A1* | 3/2009 | Weitz | G01N 33/5052 424/130.1 |

(Continued)

OTHER PUBLICATIONS

Tovar et al, "Acoustic Cavity Transducers for Manipulation of Cells and Biomolecules", Proceedings of SPIE, Feb. 12, 2010, vol. 7574.
(Continued)

*Primary Examiner* — Dean Kwak
(74) *Attorney, Agent, or Firm* — Knobbe, Martens, Olson & Bear, LLP

(57) ABSTRACT

A method of encapsulating a solid sample in a droplet, the method including flowing a continuous phase through a first fluid channel at a first flow rate; flowing a dispersed phase through a second fluid channel at a second flow rate, the dispersed phase including a plurality of particles, cells or beads; trapping the plurality of particles, cells or beads in a mixing region that receives the dispersed phase and the continuous phase; and reducing the first flow rate to encapsulate the trapped particles, cells or beads in droplets of the dispersed phase generated when the dispersed phase and the continuous phase exit the mixing region through an orifice.

8 Claims, 7 Drawing Sheets

Related U.S. Application Data

(60) Provisional application No. 62/273,280, filed on Dec. 30, 2015, provisional application No. 62/273,131, filed on Dec. 30, 2015.

(51) Int. Cl.
| | | |
|---|---|---|
| *C12N 11/04* | (2006.01) | |
| *B01F 33/3011* | (2022.01) | |
| *G01N 1/38* | (2006.01) | |
| *B01F 23/41* | (2022.01) | |
| *B01F 31/00* | (2022.01) | |
| *B01F 31/65* | (2022.01) | |

(52) U.S. Cl.
CPC .......... *B01F 31/65* (2022.01); *B01F 33/3011* (2022.01); *C12N 5/0012* (2013.01); *C12N 11/04* (2013.01); *B01L 2200/0636* (2013.01); *B01L 2200/0647* (2013.01); *B01L 2200/0673* (2013.01); *B01L 2300/0867* (2013.01); *B01L 2400/0439* (2013.01); *B01L 2400/0487* (2013.01); *G01N 1/38* (2013.01)

(58) Field of Classification Search
CPC ..... B01L 2200/0636; B01L 2200/0652; B01L 3/502761; B01L 2300/0816; B01L 2200/0647; B01L 2200/0673; B01L 2200/10; B01L 2300/0861; B01L 2400/0436; B01F 3/0807; B01F 11/0071; B01F 11/0077; B01F 13/0062; C12N 5/0012; C12N 11/04; G01N 1/38; G01N 2015/149
USPC ...................... 422/502–504, 73; 436/10, 180
See application file for complete search history.

(56) References Cited

U.S. PATENT DOCUMENTS

| | | | |
|---|---|---|---|
| 2011/0030808 A1* | 2/2011 | Chiou | ................ F16K 99/0061 137/13 |
| 2014/0011291 A1 | 1/2014 | Patel et al. | |
| 2015/0017678 A1 | 1/2015 | Matula et al. | |
| 2015/0219623 A1 | 8/2015 | Doria et al. | |
| 2017/0241878 A1* | 8/2017 | Broyer | ............. G01N 27/44704 |

OTHER PUBLICATIONS

Tovar et al. 2009 "Lateral Cavity Acoustic Transducer", *Lab on a Chip* 9: 41-43.

* cited by examiner

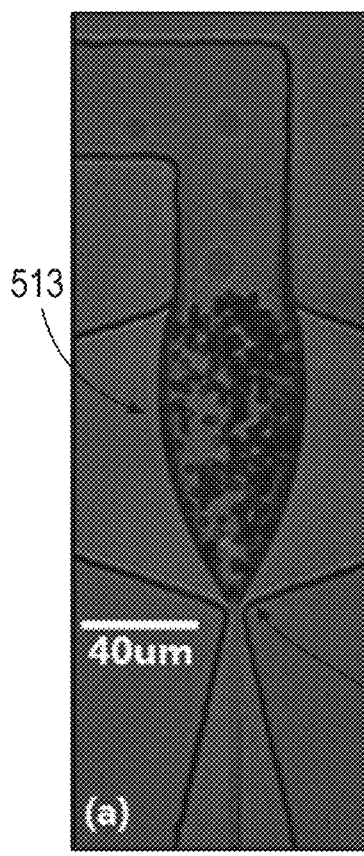 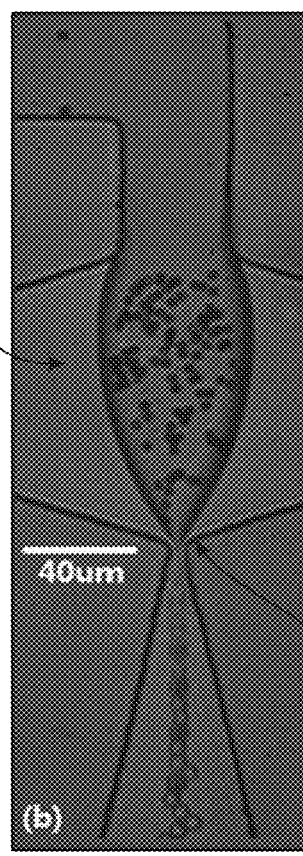 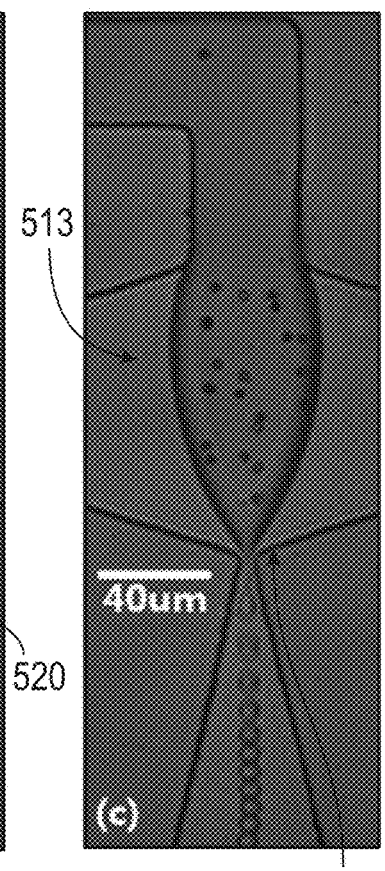
FIG. 9A  FIG. 9B  FIG. 9C
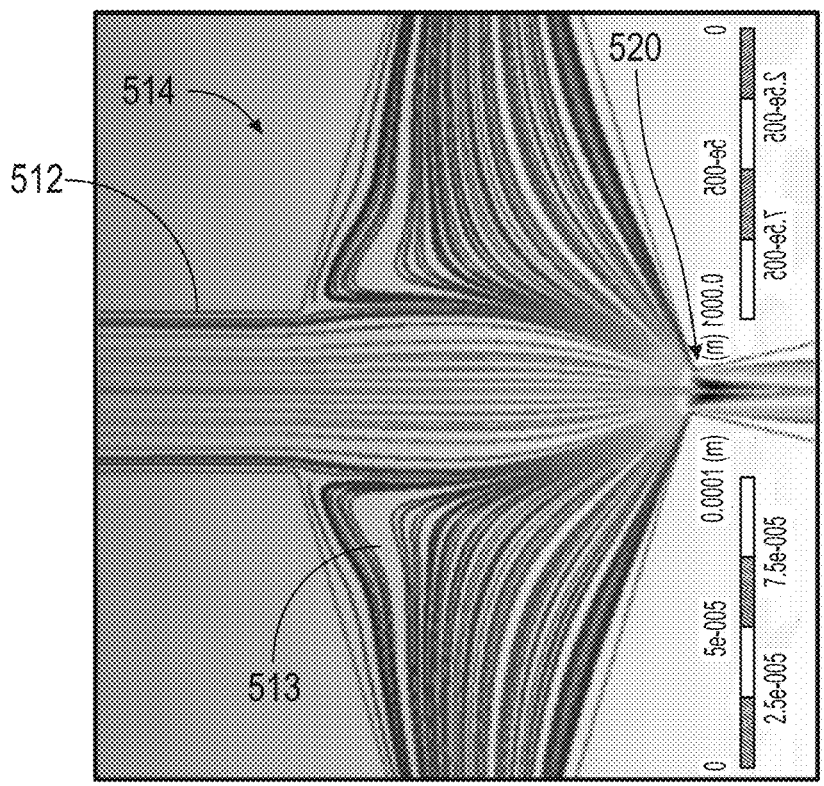
FIG. 10

025# ENHANCED CELL/BEAD ENCAPSULATION METHODS AND APPARATUSES

STATEMENT REGARDING FEDERALLY SPONSORED R&D

The inventions were made with government support under Grant No. 1362165 awarded by the National Science Foundation. The government may have certain rights in the inventions.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND

Field of the Invention

This disclosure relates generally to microfluidic devices.

Description of the Related Art

Microfluidic devices and systems are configured to process (e.g., move, mix, separate) small volumes of fluid. Microfluidic devices and systems are used for various applications including printing, bio-chemical assays, drug discovery, etc. A class of microfluidic devices and systems includes microfluidic droplet generating and manipulating devices. Droplet-based microfluidic devices and systems are compatible with many chemical and biological reagents. Droplet-based microfluidic devices can be configured to manipulate discrete droplets. Droplet-based microfluidic devices can be configured to perform a variety of operations, such as, for example, transportation of droplets, storage of droplets, mixing of droplets, analysis of droplets, etc. Droplet-based microfluidic devices can be configured to perform a variety of operations repeatably using a set of programmable instructions. Accordingly, droplet-based microfluidic devices can be also be referred to as digital microfluidic devices. Droplet-based microfluidic devices can be used in a variety of applications including but not limited to as microreactors to achieve controlled and rapid mixing of fluids and/or to synthesize particles and encapsulate many biological entities for biomedicine and biotechnology applications.

SUMMARY

Example embodiments described herein have several features, no single one of which is indispensable or solely responsible for their desirable attributes. Without limiting the scope of the claims, some of the advantageous features will now be summarized.

Various embodiments discussed herein include droplet-based microfluidic devices that rely on trapped air bubbles in liquid to disrupt particle-trapping vortices and facilitate cell/bead encapsulation. As microfluidic droplet production rate is increased, and size is decreased, incoming cells/beads tend to become trapped in microvortices in the flow-focusing region, instead of being encapsulated in the droplets. To disrupt the microvortices in the flow-focusing region, an air cavity is integrated in the droplet generation region of a microfluidic device. The air cavity can be integrated upstream from an orifice of the flow-focusing region that generates the liquid droplets. During droplet generation, the air trapped in the structure can be vibrated. The vibrations can produce vortices that flow counter to the microvortices produced in the flow-focusing region of the microfluidic device. Accordingly, devices including the concepts described herein can reduce cell/bead trapping upstream from the orifice of the flow-focusing region and improve encapsulation efficiency.

Various embodiments discussed herein include a microfluidic device comprising an acoustically resonant structure that can improve cell/bead encapsulation efficiency. It may be possible to switch between a cell/bead trapping mode in which cells/beads are trapped upstream from an orifice of the flow-focusing region, and an encapsulating mode in which the cell/bead are encapsulated in droplets by controlling piezoelectric transducer activation. The embodiments described herein can increase the percentage of cells/beads encapsulated in droplets which can be useful in the field of single cell and single analyte assays. Single cell assay platforms with vibrating air cavities controlled by piezoelectric transducer can be easier to use and cheaper to manufacture than single cell assay platforms that rely on magnetic bead or cytometry-based switching approaches. Single cell assay platforms with vibrating air cavities controlled by piezoelectric transducer can also improve the percentage of cells/beads that are encapsulated in droplets over existing methods (e.g., magnetic bead or cytometry-based approaches) that may affect outcome of single cell assays. Single cell assay platforms with vibrating air cavities controlled by piezoelectric transducer can be used to carry out genotyping or gene sequencing on single cells.

Various embodiments discussed herein comprise microfluidic devices that are configured to encapsulate single particle or cells with high through-put. Various embodiments of the microfluidic devices can be configured to provide encapsulation efficiency of 30% or higher. For example, various microfluidic devices discussed herein can be configured to encapsulate particles or cells having a size of about 2.5 μm with encapsulation efficiency of about 30% or greater in less than 1 second. Various innovative aspects of the subject matter of this application rely on various principles governing size based trapping in droplet generation region. Various embodiments of microfluidic devices discussed herein employ a simple trapping-encapsulating method to enhance the encapsulation efficiency with a low concentration of particles in the dispersed phase. Various embodiments of microfluidic devices discussed in this application can be configured as sorting devices that are capable of sorting droplets with particles and without particles.

One innovative aspect of the subject matter described in this disclosure can be implemented in a microfluidic device, comprising a first fluid channel configured to transport a first fluid; a second fluid channel configured to transport a second fluid; an output fluid channel disposed downstream from the first and the second fluid channels; and a flow-focusing region, the first and the second fluid channels terminating in the flow-focusing region. The flow-focusing region comprises an orifice disposed to output the first and the second fluids transported through the first and the second fluid channels into the output fluid channel. The flow-focusing region also can include a fluid controller that is configured to control the flow rate and/or disrupt vortices. For example, the fluid controlled can be configured to adjust the fluid pressure of the first and/or the second fluid such that particles or cells dispersed in the first or the second fluid can be trapped in a first mode and encapsulated in droplets of the first or the second fluid in a second mode. In various embodiments, the fluid controller can be configured to vibrate an air cavity placed upstream from the orifice. The air cavity can be vibrated to modulate the flow rate. In other embodiments the flow rate can be modulated in other ways, such as by restricting or widening the passage upstream of the orifice or by modulating the flow generating device, e.g., a pump device. The microfluidic device can further comprise a piezo-electric transducer configured to vibrate the air cavity.

One innovative aspect of the subject matter described in this disclosure can be implemented in a method of encapsulating a solid sample in a droplet. The method comprises flowing a first fluid through a first fluid channel, the first fluid including the solid sample (e.g., particle/cell/bead); flowing a second fluid through a second fluid channel; forcing the first and the second fluids through an orifice into an output fluid channel; and modulating a fluid flow parameter in a zone upstream from the orifice. A flow rate of the second fluid is configured to generate droplets of the first fluid of a desired size, and the fluid flow parameter is configured to achieve a desired encapsulation efficiency. The fluid flow parameter can be a vibration parameter and the modulating can involve vibrating an air cavity. The fluid flow parameter can be a flow rate parameter and the modulating can involve altering the fluid flow rate upstream from the orifice. In various embodiments, a piezo-electric transducer can be configured to vibrate the air cavity. In various embodiments, the solid sample can comprise a cell or a bead including an organic material. The parameter can be a frequency of vibration or an amplitude of vibration.

Another innovative aspect of the subject-matter described in this disclosure can be implemented in a microfluidic device including one or more outer channels configured to transport a first fluid towards an output channel and one or more inner channels configured to transport a second fluid towards the output channel. The microfluidic device comprises a fluid control system to control the flow rate of the first fluid through the outer channels in order to first trap particles/cells/beads that are larger than a certain size (or diameter) immersed in the second fluid. If the flow rate of the first fluid is above a certain flow rate, two symmetric vortices (or microstreaming) form right before the orifice in the second fluid streaming through the inner channels. The inner channels contain the particles/cells/beads. These vortices can trap particles/beads/cells above a certain size and allow smaller ones to leak through a gap between the vortices and the channel walls having a dimension $d_{gap}$. If a particle/bead/cell has a radius larger than the $d_{gap}$, the probability that the particle/bead/cell is trapped in the vortices is high. Accordingly, the fluid control system can be configured to control the flow rate of the first fluid such that vortices are formed, then the particles/beads/cells in the second fluid can be trapped. The fluid control system can be configured to lower the flow rate of the first fluid such that the size of the vortices is reduced or the vortices may not be even formed so as to allow incoming particles/beads/cells to flow through the orifice into the output channel. By controlling the flow rate of the first fluid, the incoming particles/beads/cells can be encapsulated in droplets of the second fluid that are formed when the second fluid is forced through the orifice in the output channel. In this manner, the flow control system can be used to switch the microfluidic device between a trapping mode and an encapsulation mode. By accumulating solid sample (e.g., particles/beads/cells) in the trapping mode first and then releasing the solid sample (e.g., particles/beads/cells) in the encapsulation mode, higher percentage of encapsulation a single particle/cell/bead in a single droplet is made possible.

One innovative aspect of the subject matter of this application is embodied in a microfluidic device, comprising: a first fluid channel configured to transport a continuous phase; a second fluid channel configured to transport a dispersed phase, the dispersed phase comprising a solid sample having a plurality of particles; a droplet generation region; and a fluid controller. The droplet generation region comprises a mixing region configured to receive the continuous phase and the dispersed phase; and an output fluid channel connected to the mixing region through an orifice. The fluid controller is configured to adjust at least one flow parameter of the continuous phase or the dispersed phase to trap the plurality of particles of the dispersed phase in the mixing region in a first mode such that the plurality of particles of the dispersed phase are prevented from flowing through the orifice. The fluid controller is further configured to adjust at least one flow parameter of the continuous phase or the dispersed phase to allow the plurality of particles to flow through the orifice such that the plurality of particles are encapsulated in droplets of dispersed phase in a second mode.

In various embodiments of the microfluidic device, the at least one flow parameter can include a flow velocity and/or a fluid pressure. In the first mode, the fluid controller can be configured to adjust at least one flow parameter of the continuous phase or the dispersed phase to generate a vortex in a flow field of the dispersed phase in the mixing region. In the first mode, the fluid controller can be configured to adjust at least one flow parameter of the continuous phase or the dispersed phase such that a distance ($d_{gap}$) between an outermost streamline of the vortex generated in flow field of the dispersed phase and an interface between the dispersed phase and the continuous phase is greater than or equal to a size of the plurality of particles. In the second mode, the fluid controller can be configured to adjust at least one flow parameter of the continuous phase or the dispersed phase to dissipate vortices in a flow field of the dispersed phase in the mixing region. In various embodiments, the continuous phase can comprise a lipid and/or the dispersed phase can comprises an aqueous material. In various embodiments, the plurality of particles can comprise biological cells or molecules. The size of the plurality of particles can be about 2.5 µm.

Various embodiments of the microfluidic device can further comprise a third fluid channel configured to allow the flow of a buffer solution through the mixing region. A parameter of the flow of the buffer solution can be controlled by the fluid controller to untrap particles having a size smaller than a desired size from the plurality of particles.

One innovative aspect of the subject matter of this application includes a method of encapsulating a solid sample in a droplet. The method comprises: flowing a continuous phase through a first fluid channel at a first flow rate; flowing a dispersed phase through a second fluid channel at a second flow rate, the dispersed phase comprising particles or cells; trapping the particles or cells in a mixing region that receives the dispersed phase and the continuous phase; and reducing the first flow rate to encapsulate the trapped particles or cells in droplets of the dispersed phase generated when the dispersed phase and the continuous phase exit the mixing region through an orifice. A size of the particles or cells can be less than or equal to a distance ($d_{gap}$) between an outermost streamline of a vortex formed in flow field of the dispersed phase and an interface between the dispersed phase and the continuous phase.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of the drawings.

FIG. 9A shows particles or cells trapped in the droplet formation region of a microfluidic device. FIG. 9B shows the encapsulation of the particles or cells in single droplets. FIG. 9C shows the particles or cells approximately 1 second after encapsulation as depicted in FIG. 9B.

FIG. 10 illustrates a simulation of fluid flow through an embodiment of a microfluidic device.

DETAILED DESCRIPTION OF THE PREFERRED EMBODIMENT

This application is directed to improve cell/bead encapsulation efficiency using flow parameter modulation such as with a fluid controller that is configured to vary flow velocity and/or fluid pressure or an acoustically resonant structure that reduces cell/bead trapping in a flow-focusing region of a droplet generation region of a microfluidic device.

Lateral Cavity Acoustic Transducer (LCAT)

The lateral cavity acoustic transducer (LCAT) is a microfluidic actuator configured to carry out diverse functions such as microfluidic pumping, mixing, and particle trapping.

Figure 1A:
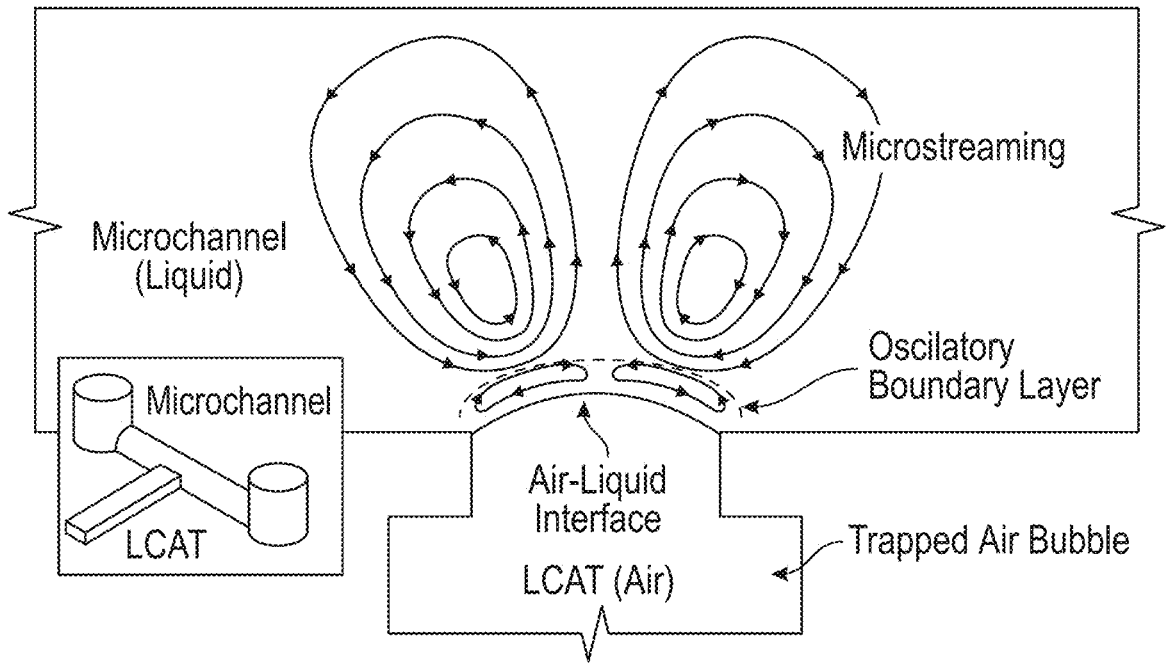
FIGS. 1A and 1B illustrate embodiments of a microfluidic device including lateral cavity acoustic transducers (LCATs) that are configured to manipulate fluids.
Figure 1B:
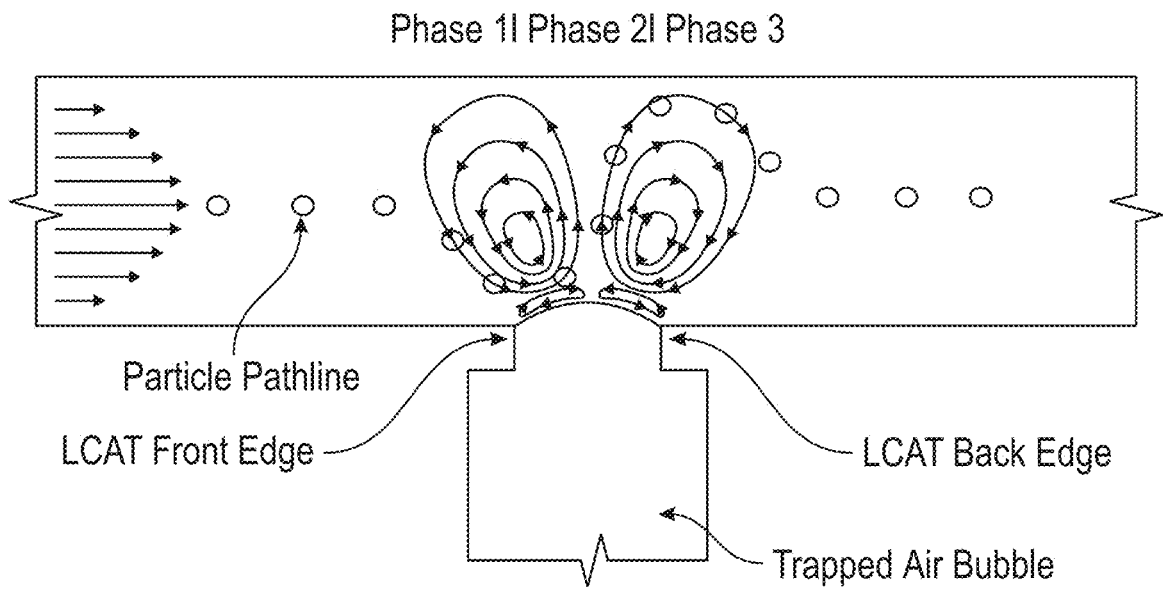

The LCAT is based on a phenomenon that uses trapped air bubbles in liquid for various applications including but not limited to pumping, mixing, particle trapping, particle sorting, bead deflection, etc. The air bubbles are trapped in sidewall lateral cavities and are excited by an external acoustic field which causes the liquid/air interface to resonate. As the air/liquid interface resonates, a net force is produced out of the end of the cavity. By controlling the angle of these cavities, different fluidic operations can be performed. For example, by orienting the LCATs at an oblique angle to the microfluidic channel, fluid pumping or propulsion can be accomplished. As another example, by orienting the LCATs perpendicular to the microfluidic channel, fluid mixing can be accomplished. FIGS. 1A and 1B illustrate embodiments of a microfluidic device including LCATs that are configured to manipulate fluids. Without subscribing to any theory, exciting the trapped air bubbles in the LCATs by an acoustic field can induce microstreaming in the microfluidic channel that can be used for various applications including but not limited to pumping, mixing, particle trapping, particle sorting, bead deflection, etc.

In various implementations, the air bubbles trapped in the sidewall lateral cavities can be excited using piezo-electric transducers. In such implementations, the vibrating air cavity/bubble can induce microstreaming of the liquid flowing through the microfluidic channel.

Microfluidic Droplet Generators

Figure 2:
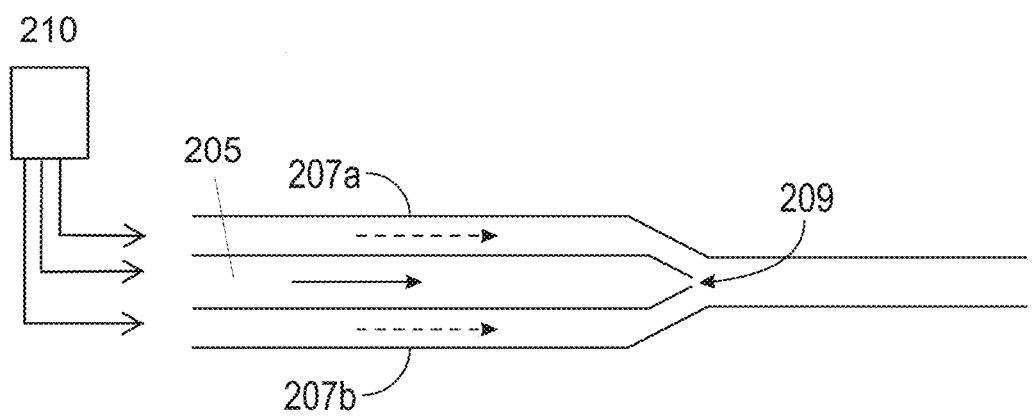
FIG. 2 schematically illustrates an embodiment of a microfluidic device including a flow-focusing droplet generator.
Figure 3:
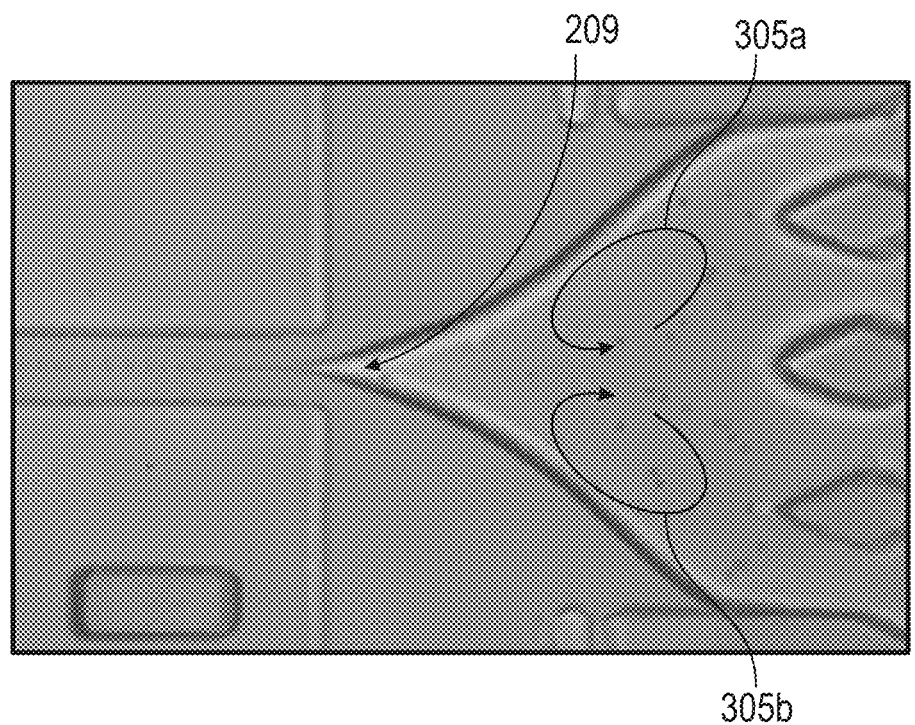
FIG. 3 illustrates the vortices generated in the flow-focusing region around the orifice of an embodiment of a microfluidic device.

Microfluidic devices including droplet generation portions can be used to create droplets of a fluid (e.g., oil or water). Microfluidic devices that include droplet generation portions can be used: to study chemical reactions, in drug delivery, in drug discovery, etc. One method of generating droplets in microfluidic devices uses flow focusing. FIG. 2 schematically illustrates an embodiment of a microfluidic device including a flow-focusing droplet generator. The flow-focusing droplet generator generates droplets by flowing a first liquid (e.g., water) through the channel 205 and a second liquid (e.g., oil) through the channels 207a and 207b. Pump and/or pressure regulator 210 is configured to control flow rate or pressure of the first liquid through channel 205 and/or the second liquid through channels 207a and 207b. The first and the second liquid streams are forced through an orifice 209. The first liquid flowing through the channel 205 (e.g., water) is broken up to form discrete droplets as a result of shear forces. The size of the generated first liquid droplets generated can depend on a variety of factors including velocity of the second liquid. For example, as the velocity of the second liquid is increased, the size of the first liquid droplets is reduced. As the rate of droplet generation is increased and/or the size of the droplets is decreased, vortices (e.g., microvortices) can be generated in the flow-focusing region around the orifice 209. FIG. 3 illustrates the vortices 305a and 305b generated in the flow-focusing region around the orifice 209 of an embodiment of a microfluidic device.

The flow-focusing droplet generator can also be used to compartmentalize or encapsulate a single cell or a bead comprising single cell, cellular material or some other biological material in a single water droplet. Droplets encapsulating a single cell or bead can be useful for single cell assays of cells (e.g., cancer cells or immune cells) that exhibit biological heterogeneity for which assays that provide a population average may be insufficient. As the rate of droplet generation is increased and/or the size of the droplets is decreased, incoming cells and/or beads may get trapped in the vortices that are generated in the flow-focusing region around the orifice 209 and not be encapsulated in droplets. This may result in a decrease in the percentage of cells or beads that are encapsulated in the droplets. This disclosure contemplates positioning a vibrating air cavity in the flow-focusing region upstream from the orifice 209 to disrupt the particle-trapping vortices and facilitate cell/bead encapsulation. The vibrating air cavity can produce vortices in the flow-focusing region around the orifice 209 that are in a direction opposite to the direction of the vortices produced in the flow-focusing region around the orifice 209 as a result of increase in rate of droplet generation and/or decrease in the size of the generated droplets.

Figure 4:
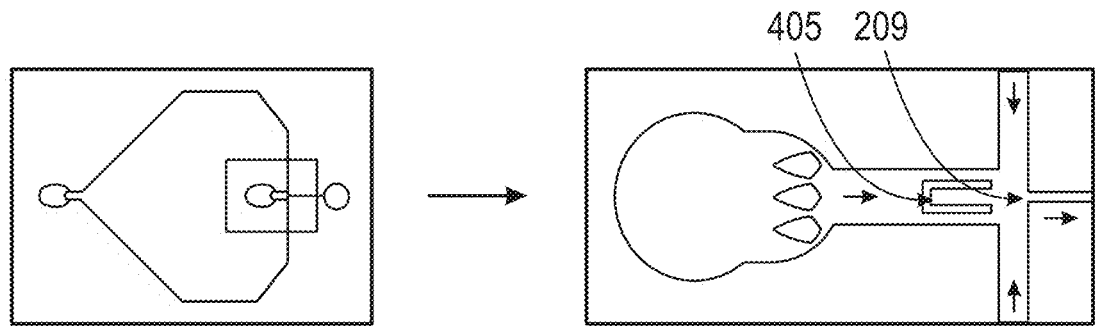
FIG. 4 schematically illustrates a design of an embodiment of a microfluidic droplet generating device including an air cavity configured to disrupt vortices.

FIG. 4 illustrates a device design created in L-Edit and Adobe Illustrator, and sent to CadArt Services to be printed as a 20 k DPI transparency mask. The mask was used to create an SU-8 mold on a silicon wafer. The mold, in turn, was used to cast devices made of PDMS elastomer. Liquids are flowed into the device through Tygon tubing, with flows controlled by either Harvard syringe pumps or pressure regulators. Air is caught in the structure 405 upstream from the orifice 209 as the device is filled with liquid. During droplet generation, the air trapped in the cavity 405 is vibrated by placing the device on a piezo-electric transducer driven with a function generator and amplifier. As discussed above, the vibrations can produce vortices that flow counter to the vortices in front of the orifice, allowing incoming cells/beads to enter the produced droplets. Vibration parameters such as amplitude and/or frequency can be adjusted to disrupt vortices that may be generated in the flow-focusing region. The device design illustrated in FIG. 4 and the device discussed above can reduce cell/bead trapping upstream from the orifice and improve/increase encapsulation efficiency. The device design illustrated in FIG. 4 and the device discussed above can also facilitate switching between trapping and encapsulating modes by controlling piezoelectric transducer activation. As discussed below, the functionality of switching between trapping and encapsulating modes can be advantageous in reducing the number of droplets that do not include any cells or include multiple cells.

An objective of droplet microfluidic systems and devices is to direct molecules, particles or cells at a one-to-one ratio as droplets are generated in microchannels. The process of loading particles or cells into drops can be random and dictated by Poisson statistics. The probability of a drop containing k cells is $(\lambda^k e^{-\lambda})/k!$' where $\lambda$ is the average number of particles or cells per drop. Thus, the ratio of drops containing one particle or cell to those containing two particles or cells is $2/\lambda$. In order to reduce the number of drops that contain more than a single particle or cell the average loading densities should be reduced. This can increase the probability that many drops may encapsulate no particles or cells. Thus, in accordance with Poisson's stochastic distribution, the resultant encapsulations are either ones with multiple particles per droplet or ones with many empty droplets. Recent research indicates that there is a size separation similar to LCAT vortices. Thus integrating air cavities (e.g., LCATs) with droplet microfluidic systems can be advantageous in overcoming the limitation of Poisson distribution (large number of empty droplets). For example, the cell/bead encapsulation efficiency can be increased by switching flow rate regimes away from flow rates at which cells/beads are trapped/accumulated to flow rates at which cells/beads are released/encapsulated. The switching of the flow rates can be accomplished by controlling the piezoelectric transducer that excites the air cavity/bubbles in the LCATs.

Figures 5A, 5B:
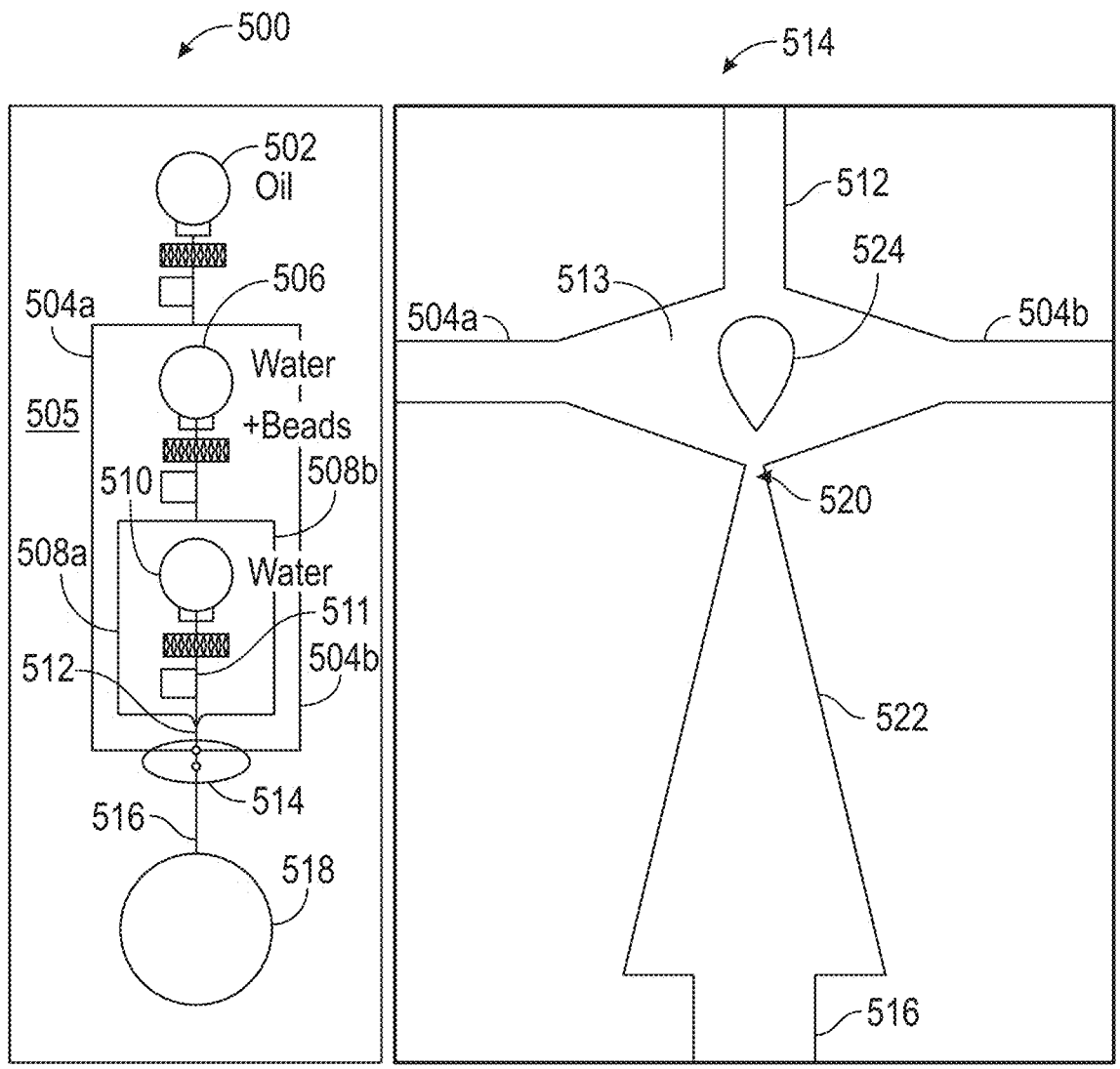
FIG. 5A illustrates an embodiment of a microfluidic device that is configured to encapsulate particles or cells in droplets of a dispersed phase that are suspended in a continuous phase.
FIG. 5B illustrates details of the droplet generation region of the microfluidic device depicted in FIG. 5A.

FIG. 5A illustrates an embodiment of a microfluidic device 500 that can encapsulate particles or cells in droplets of a dispersed phase that are suspended in a continuous phase. The continuous phase and the dispersed phase comprise immiscible materials. For example, in some embodiments the continuous phase can comprise a lipid and the dispersed phase can comprise an aqueous material. As another example, in some embodiments the continuous phase can comprise an aqueous material and the dispersed phase can comprise a lipid.

In the illustrated embodiment, the microfluidic device 500 includes a first inlet 502 for introducing a first material that provides the continuous phase, a second inlet 506 for introducing a second material that is immiscible in the first material and provides the dispersed phase, a droplet generating region 514 and an outlet 518. The second material also includes a solid sample (e.g., particles or cells or beads) that are to be encapsulated. In various embodiments, a lipid phase (e.g., an oil, a fatty acid, etc.) can be introduced through the first inlet 502 and an aqueous phase (e.g., water) including the solid sample (e.g., particles or cells or beads) can be introduced through the second inlet 506. In various embodiments, the dispersed phase can comprise blood and the continuous phase can comprise materials that have appropriate viscosity and provide equilibrium surface tension between the continuous and dispersed phases such that droplets are formed in the dripping regime as discussed below. The first material (e.g., a lipid or an aqueous material) introduced through the first inlet 502 is transmitted towards the droplet generating region 514 through the microfluidic channels 504a and 504b and the second material (e.g., an aqueous material or a lipid) including the solid sample (e.g., particles or cells or beads) introduced through the second inlet 506 is transmitted towards the droplet generating region 514 through microfluidic channels 508a, 508b and 512. FIG. 5B illustrates the details of the droplet generating region 514. The droplet generating region 514 includes a mixing region 513 that is fluidically connected to an enlarged region 522 through an orifice 520, and an outlet microfluidic channel 516 connected to the outlet 518. The first and the second materials (e.g., aqueous material and the lipid) enter the enlarged region 522 through the orifice 520 and droplets of the second material (e.g., aqueous material) are formed in the first material (e.g., lipid) as the first and the second materials exit through the orifice 520.

As depicted in FIG. 5B, the droplet generating region 514 further includes a post 524 that is configured to change the flow field (e.g., change the direction of flow of the first and the second material, change the flow velocity of the first and the second material or both) and/or decrease the vortex sizes in the droplet generation region 514.

Referring back to FIG. 5A, the microfluidic device 500 further comprises a buffer region that includes a third inlet 510 for introducing a buffer solution (e.g., water) and microfluidic channel 511. The solid sample (e.g., particles or cells or beads) introduced through the second inlet 506 can be encapsulated in droplets of the second material that are formed as the first and the second materials exit through the orifice 520.

Flow parameters (e.g., flow velocity and/or fluid pressure) of the continuous and/or the dispersed phase can be adjusted to trap the solid sample (e.g., particles, cells or beads) introduced through the second inlet 506 are trapped in the mixing region 513. A buffer solution (e.g., water) can be made to flow through the mixing region 513. The flow parameters (e.g., flow velocity and/or fluid pressure) of the buffer solution can be adjusted to wash away unwanted portions of the solid sample (e.g., particles, cells or beads having a size less than a desired size) and/or debris from the trapping vortices that are configured to trap the solid sample (e.g., particles or cells or beads). After the vortices have been washed, the flow parameters (e.g., flow velocity and/or fluid pressure) of the continuous and/or dispersed phase can be adjusted to release the desired portion of the solid sample (e.g., particles or cells or beads of a desired size) such that the desired portion of the solid sample can be encapsulated in droplets of the second material. In various embodiments, the trapping of the desired portions of the solids sample and washing of the vortices by the buffer solution can advantageously increase the concentration of the desired portion of the solid sample. Various embodiments of the microfluidic device can be configured to intermittently switch between flowing the dispersed phase and flowing the buffer solution. Switching between flowing the dispersed phase and the buffer solution can be advantageous in flushing the vortices to remove particles having undesirable size and debris and to increase concentration of particles having desirable size as discussed above. Another advantage of switching between flowing the dispersed phase and the buffer solution can be to prevent oversaturation of the vortices.

The microfluidic device can include a fluid controller that is configured to control various fluid parameters of the buffer solution, the first material, the second material and/or the particle or cells. For example, the fluid controller may be configured to control the flow rates of the first material, the second material and/or the particle or cells. As another example, the fluid controller may be configured to control the fluid pressure of the first material, the second material and/or the particle or cells.

The fluid flow of the first material and the second material through the microfluidic channels of the microfluidic device 500 can be simulated using a computer program (e.g., Fluent). The fluid flow of the first and the second materials can be simulated by considering the flow as a 2D geometry. Depending on the flow velocity of the first and the second materials two kinds of flow fields are generated—a flow field with vortex and a flow field without vortex.

When the pressure of external phase (e.g., continuous phase or first material) is relatively high, the velocity of external phase (e.g., continuous phase or first material) can also be large. This in turn can make the velocity of the internal flow (e.g., the dispersed phase or the second material with or without the particles or cells) near the interface large as well. When the flow rate of the internal flow (e.g., the dispersed phase or the second material with or without the particles or cells) near the interface is equal to the flow rate of internal phase droplets (e.g., droplets of the dispersed phase or droplets of the second material with or without the particles or cells) at or near the orifice 520, vortices can be formed in the flow field of the internal phase (e.g., the dispersed phase or the second material with or without the particles or cells) in the droplet generation region 514 (e.g., in the mixing region 513). The formation of the vortices may reduce the flow rate of the internal phase (e.g., the dispersed phase or the second material with or without the particles or cells) at the orifice 520.

When the pressure of external phase (e.g., continuous phase or first material) is relatively low, the flow rate of internal flow (e.g., the dispersed phase or the second material with or without the particles or cells) near the interface is less than the flow rate of internal-phase droplets (e.g., droplets of the dispersed phase or droplets of the second material with or without the particles or cells) at or near the orifice 520 such that no vortices are generated at or near the orifice 520 and the flow rate of the internal flow (e.g., the dispersed phase or the second material with or without the particles or cells) towards the orifice 520 may not be reduced.

Figure 6A:
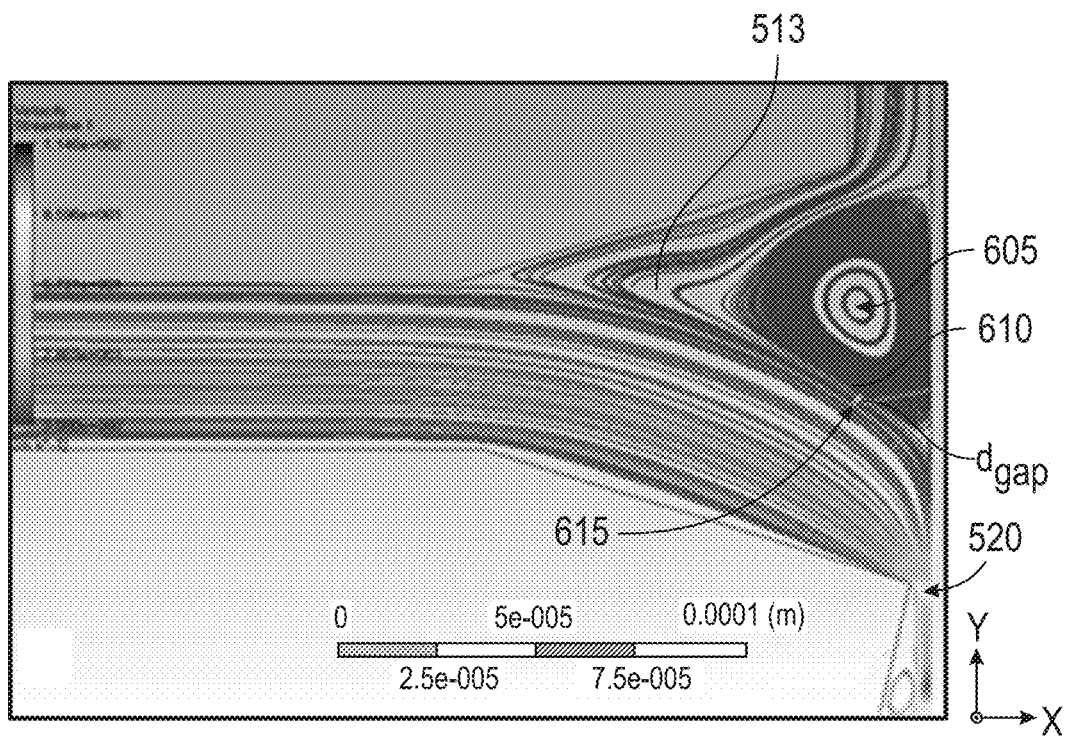
FIG. 6A is a simulation showing the generation of vortices in the droplet generation region of an embodiment of a microfluidic device.
Figure 6B:
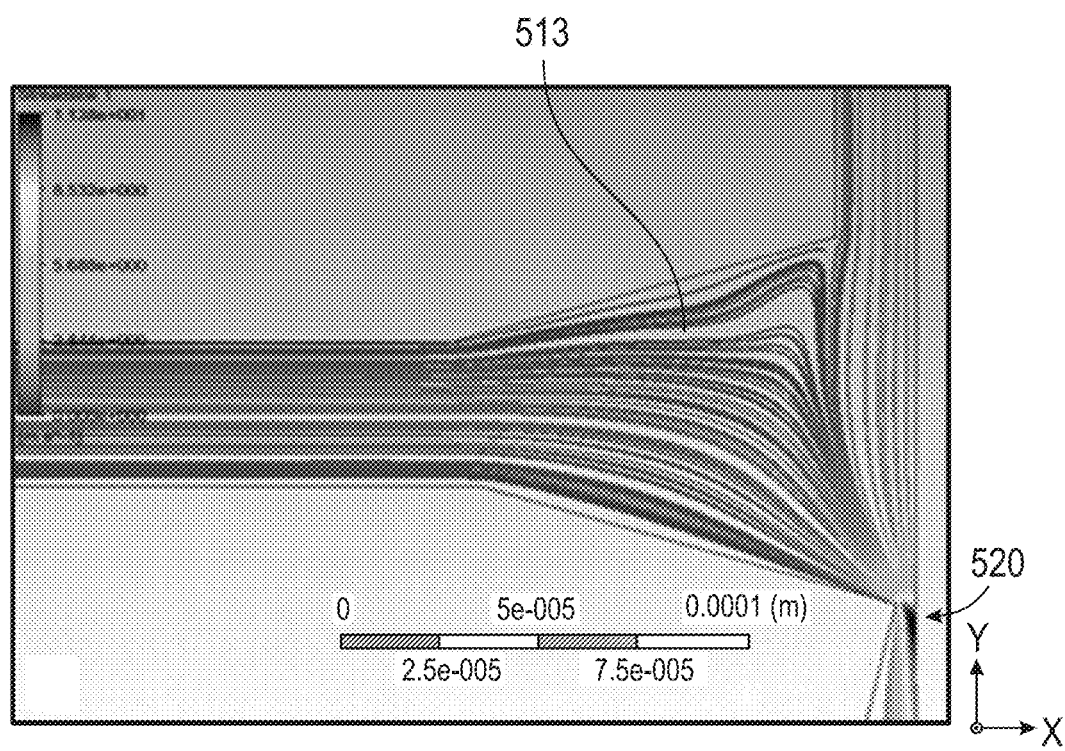
FIG. 6B is a simulation showing streamline fluid flow in the droplet generation region of an embodiment of a microfluidic device.

FIG. 6A shows the generation of vortices 605 in the fluid flow of the dispersed phase or the second material with or without the particles or cells in the droplet generation region 514 when the pressure of the continuous phase or the first material is high and FIG. 6B shows a streamlined fluid flow (e.g., without vortices) of the dispersed phase or the second material with or without the particles or cells in the droplet generation region 514 when the pressure of the continuous phase or the first material is low.

The particles or cells introduced through the third inlet 510 will not be trapped in the mixing region 513 in the absence of any vortices in fluid flow of the dispersed phase or the second material at or near the orifice 520. However, when vortices are formed in the fluid flow of the dispersed phase or the second material at or near the orifice 520, beads may be trapped depending on the distance between the interface of the continuous and the dispersed phase and the outermost streamline of the vortex. The distance between the interface of the continuous and the dispersed phase—indicated by reference numeral 615 in FIG. 6A and the outermost stream-line 610 of the vortex 605 is referred to herein as $d_{gap}$. The distance between the interface of the continuous and the dispersed phase and the outermost stream-line of the vortex $d_{gap}$ can depend on the flow velocities of the continuous and the dispersed phases. When the radius of particles or cells is greater than $d_{gap}$, the center of the particles or cells will cross into a closed streamline (e.g., a streamline of the vortex) increasing the probability that the particles or cells are trapped in the mixing region 513. However, when the radius of particles or cells is less than $d_{gap}$, some particles or cells may be trapped for some time in the mixing region 513 due to inertia of the particles or cells or some other forces. But these particles or cells may eventually go through the orifice 520 sometime after they have been trapped.

Figure 7:
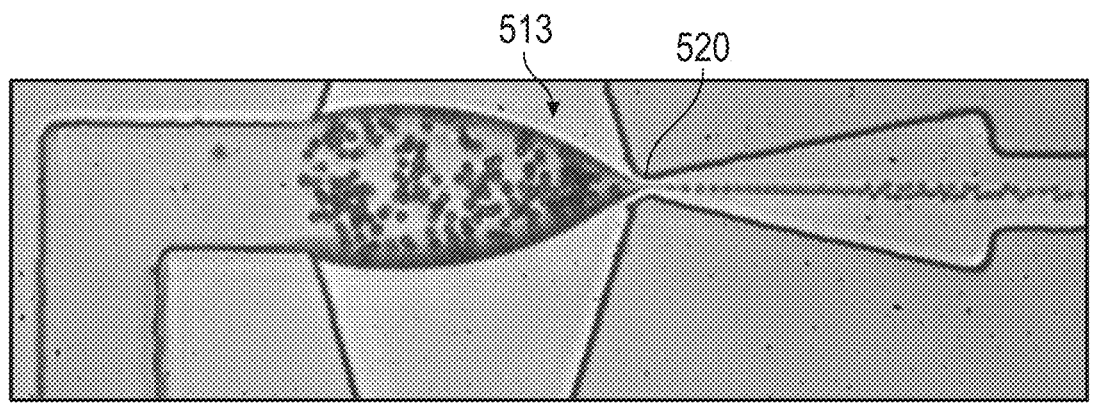
FIG. 7 illustrates an embodiment of a microfluidic device in which the particles or cells are trapped in the droplet generation region.

FIG. 7 illustrates an embodiment of a microfluidic device in which the particles or cells are trapped in the mixing region 513 of the droplet generation region 514 when $d_{gap}$ is less than the size (e.g., radius) of particles or cells. To increase the encapsulation efficiency of the particles or cells, it may be advantageous if the distance between the interface of the continuous and the dispersed phase and the outermost stream-line of the vortex $d_{gap}$ is greater than or equal to the size (e.g., radius) of the particles or cells.

There are mainly three kinds of droplet formation regimes: geometry-controlled region, dripping regime and jetting regime. The droplet formation regime is determined by the capillary number $Ca=\mu V/\gamma_{EQ}$, where $\mu$ is the viscosity of the continuous phase, V is the superficial velocity of the continuous phase, and $\gamma_{EQ}$ is the equilibrium surface tension between the two continuous and the dispersed phases.

Most traditional flow-focusing devices have been operated in the geometry-controlled regime, termed for the large dependence of droplet size on the smallest feature size in the device (e.g., the orifice). In this regime droplets break off from the dispersed phase finger following a protrude-and-retract mechanism. Droplets in the geometry-controlled regime can be highly monodisperse but limited in minimum size by the width of the orifice.

An increase in the capillary number Ca can lead to droplet generation in the dripping regime. This regime produces monodisperse droplets smaller than the size of the orifice due to narrowing of the dispersed phase finger. The dripping mode can be characterized by a dispersed phase tip that does not retract but rather remains at a fixed location in the orifice, generating a stream of droplets off the tip due to Rayleigh capillary instability.

A further increase in the capillary number leads to droplet generation in the jetting mode, wherein the dispersed phase finger extends far into the post-orifice channel (e.g., the enlarged region 522 and/or the channel 516). Droplets, which break off the tip of the dispersed phase finger due again to Rayleigh capillary instability, tend to be as large as or larger than the orifice width in the jetting mode and may be polydisperse.

Figure 8A:
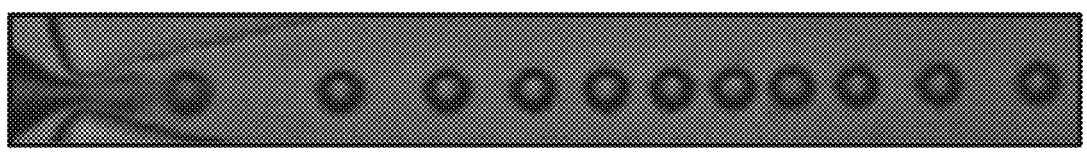
FIG. 8A shows formation of droplets in the geometry-controlled regime.
Figure 8B:
FIG. 8B shows the formation of droplets in the dripping regime.
Figure 8C:
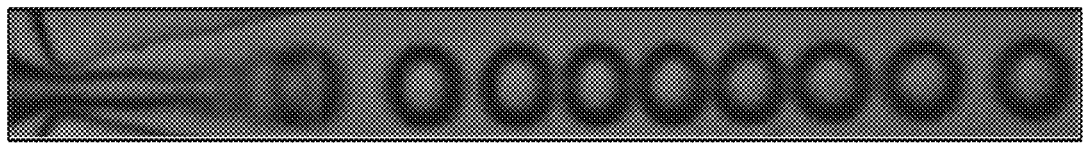
FIG. 8C shows the formation of droplets in the jetting regime.

FIGS. 8A, 8B and 8C show representative images of three distinct droplet formation regimes. FIG. 8A shows droplet formation in the geometry-controlled regime. FIG. 8B shows droplet formation in the dripping regime and FIG. 8C shows droplet formation in the jetting regime.

To encapsulate single particles or cells into one droplet, it may be advantageous if the size (e.g., the radius) of the particles or cells is almost equal to $d_{gap}$ without exceeding the size of $d_{gap}$ such that encapsulation of two or more particles into one droplet can be avoided. As discussed elsewhere herein, $d_{gap}$ sets the threshold for trapping of cells at the cell sizes of interest. With this $d_{gap}$, the cells/particles smaller than a certain size will be released in addition to concentrating the targeted cell size while the solution continues to flow through. If the radius of a bead or other solid sample is much smaller than $d_{gap}$, it is more likely for clusters of multiple beads (or other solid sample) to get caught up in one droplet as it is pinched-off (separated). On the other hand if the bead (or solid sample) radius is slightly below $d_{gap}$, only one bead (or solid sample) should be encapsulated at a time. It may be further advantageous if the value of $d_{gap}$ remained constant.

In the geometry-controlled regime, because of the protrude-and-retract mechanism, the interface of two continuous and the dispersed phases will change and vibrate during droplet formation process. This can also cause the size of the vortices and the size of $d_{gap}$ to change, which can makes it difficult to control the encapsulation.

In the dripping regime, the dispersed phase tip remains at a fixed location in the orifice, generating a stream of droplets off the tip due to Rayleigh capillary instability. The interface of the continuous and the dispersed phase can have a steady shape in the dripping regime. The size of the vortices and $d_{gap}$ can also be constant in the dripping regime. Also, the dripping regime produces very small monodisperse droplets with high throughput, which can allow $d_{gap}$ to have a value approximately equal to the size (e.g., radius) of the particles or the cells.

The interface between the continuous phase and the dispersed phase can be steady in the jetting regime. However, the size of droplets may not be constant and may be polydisperse. Thus, the dripping regime can have appropriate $d_{gap}$ for encapsulation of single particles or cells in a single droplet and also produce monodisperse droplet may be the most suitable droplet formation process for encapsulating single particles or cells in a single droplet.

To test the encapsulation performance of the microfluidic device 500 in the dripping droplet formation regime, ethyl oleate and 2% ABIL EM 90 was used as the continuous phase, and mixture of water, lipid, glycerol and surfactant was used as the dispersed phase. For example, the dispersed phase can include 5 mg DSPC (1,2-distearoyl-sn-glycero-3-phosphocholine, Avanti Polar Lipids) and 1.96 mg DSPE-PEG2000(1,2-distearoyl-sn-glycero-3-phosphoethanolamine-N-[methoxy-(polyethylene glycol)-2000], Avanti Polar Lipids) that are combined in a glass vial and dissolved in chloroform (CHCl3, Sigma) to form a homogeneous mixture. The solvent can be evaporated with a nitrogen stream. 4 mL of ultra-pure water can be added to the dry lipid mixture and sonicated at 50° C. for 20 minutes. The solution was combined with an additional 4 mL of glycerol (Sigma), and 2 mL of nonionic surfactant (Pluronic F-68, Sigma), sonicated at 50° C. for 20 minutes. The lipid solution was sonicated again for 15 minutes immediately prior to use to reduce unwanted liposome formation. The continuous phase is introduced through the first inlet 502 and the dispersed phase is added through the second inlet 510. Particles (e.g., PeakFlow™ Green flow cytometry reference beads, 2.5 µm, Molecular Probes) having a size (e.g., radius) of 2.5 µm are introduced through the third inlet 506 into the dispersed phase.

Since the high-throughput of droplet formation, normal concentration of particles in dispersed phase may cause very low encapsulation efficiency, a method to get high concentration of particles or cells in dispersed phase as described below can be used to perform encapsulation of single particles in a short time interval.

To get high concentration of particles or cells in the dispersed phase, the flow parameters (e.g., flow velocity and/or pressure of the continuous and the dispersed phases) can be adjusted using the fluid controller to generate vortices in the dispersed phase such that $d_{gap}$ is less than the size (e.g., radius) of the particles or cells so that all the particles or cells can be trapped in the mixing region 513 of the droplet generation region 514, as shown in FIG. 9A. Then the pressure of continuous phase can be reduced using the fluid controller such that $d_{gap}$ is greater than the size (e.g., radius) of the particles or cells. The particles or cells that are trapped in the droplet generation region 514 will be encapsulated in droplets in a short time interval (e.g., in less than 1 second).

FIGS. 5B and 9A shows the particles or cells trapped in the mixing region 513 of the droplet generation region 514 when $d_{gap}$ is less than the size (e.g., radius) of the particles or cells. FIGS. 5B and 9B illustrates the encapsulation process results when $d_{gap}$ is greater than the size (e.g., radius) of the particles or cells. FIGS. 5B and 9C illustrates the encapsulation of the particles or cells in droplets approximately 1 second after $d_{gap}$ is made greater than the size (e.g., radius) of the particles or cells.

With further reference to FIGS. 9A-9C, the width of the orifice (e.g., orifice 520) is approximately 4 µm. Without subscribing to any particular theory, vortices can be disrupted by adjusting the flow rate and/or fluid pressure of the continuous phase and/or the dispersed phase as discussed above. For example, as the flow rate and/or the fluid pressure of the continuous phase increases solid sample (e.g., particles/cells/beads) having a size (e.g., radius) above a threshold length are trapped and do not flow through the orifice 520. If the flow rate and/or the fluid pressure of the continuous phase is lowered below a certain threshold, the size of the vortices could reduce and/or the vortices may disappear. Under these flow conditions, the solid sample (e.g., particles/cells/beads) that were previously trapped and not allowed to flow through the orifice may flow through the orifice 520. Accordingly, in various embodiments, the flow rate and/or the fluid pressure of the continuous phase can be adjusted to reduce vortices in the flow-focusing region as shown in FIG. 10. FIG. 10 illustrates a simulation of the fluid flow in the mixing region 513 of the droplet generation region 514 (depicted in FIG. 5B) of an embodiment of a microfluidic device 500 (depicted in FIG. 5A) when the flow rate and/or the fluid pressure of the continuous phase is reduced to reduce a size of the vortices and/or to dissipate vortices. It was observed that varying the flow rate and/or the fluid pressure of the continuous phase can result in switching between trapping of the incoming solid sample (e.g., particles/cells/beads) and releasing of the incoming solid sample (e.g., particles/cells/beads) for encapsulation in droplets of the dispersed phase. As the flow rate and/or the fluid pressure of the continuous phase was adjusted to reduce vortices in the flow-focusing region trapping of the incoming solid sample (e.g., particles/cells/beads) was reduced which resulted in an increase in droplet encapsulation efficiency.

Encapsulation of particles or cells can be performed by varying initial concentration (IC) (number of particles/nL) of particles or cell in the dispersed phase, real Concentration (RC) (number of particles/nL) of trapped particles or cells in the droplet generation region before encapsulation, the initial droplet diameter (IDD) (μm) which corresponds to the diameter of droplets before encapsulation, final droplet diameter (FDD) (μm) which corresponds to the diameter of droplets after encapsulation, droplet formation frequency (DFF) (number of droplets/s) which corresponds to the number of droplets formed per second during encapsulation, encapsulation efficiency (EE) which corresponds to the proportion of droplets with particles among all droplets formed The encapsulation efficiency for different initial concentration of 6.79, 15.65, 24, 27.69, 40 number of particles/nL and for an initial droplet diameter (IDD) of about 4 μm is obtained. The initial droplet diameter (IDD) of about 4 μm can provide a $d_{gap}$ that is smaller than the size (e.g., radius) of the particles or cells and keep particles or cells from encapsulation. It is observed that the initial concentration (IC) has nearly no effect on encapsulation efficiency (EE). Instead, for certain continuous and dispersed phases and in the dripping droplet formation regime, the real concentration (RC), final droplet diameter (FDD) and droplet formation frequency (DFF) determine the encapsulation efficiency (EE).

Figure 11:
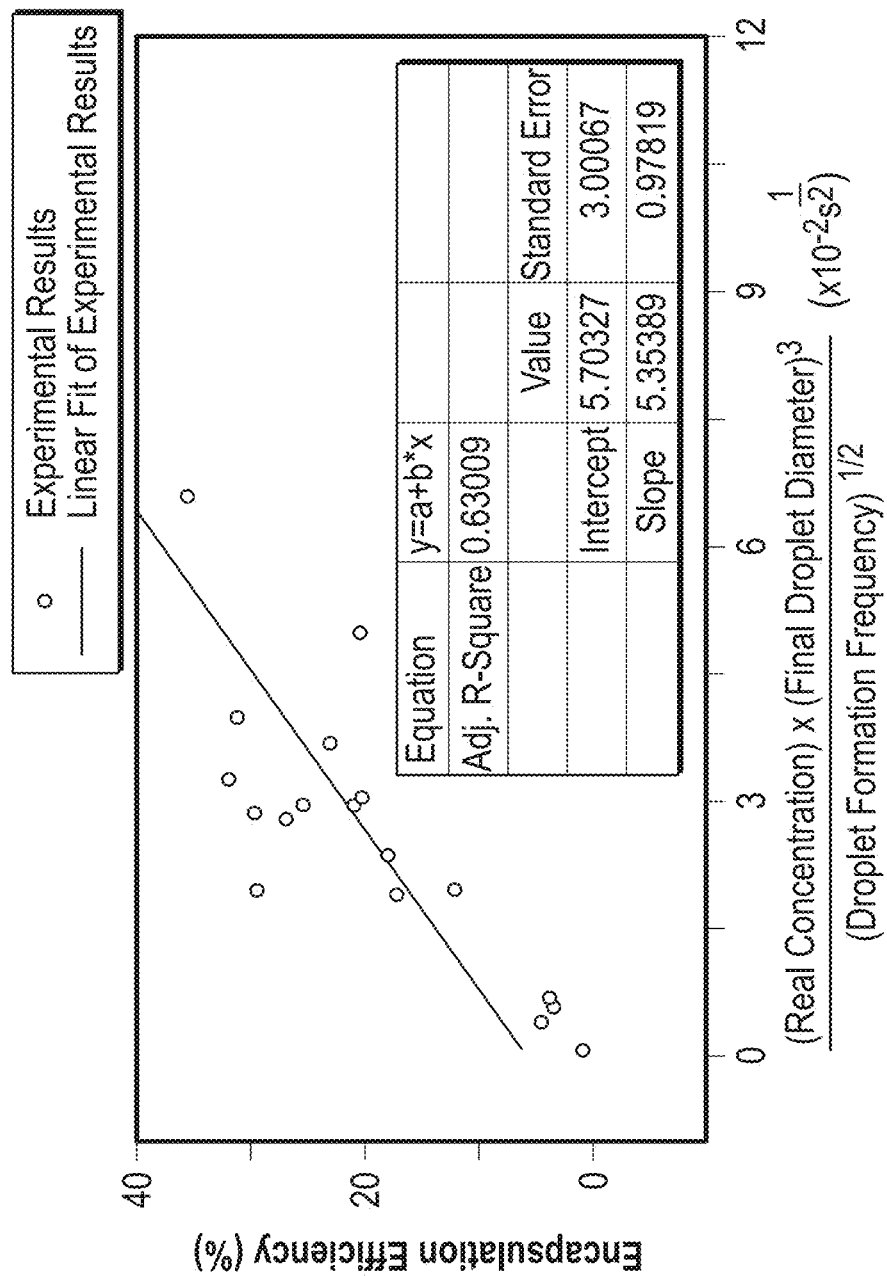
FIG. 11 is a plot of the droplet encapsulation efficiency as a function of a parameter that depends on droplet size and frequency.

FIG. 11 below shows the relationship between real concentration (RC), final droplet diameter (FDD), droplet formation frequency (DFF) and encapsulation efficiency (EE). The coefficient of determination of $$\frac{RC \times FDD^3}{DFF^{1/2}}$$

and EE is 0.63009, which indicates that the two parameters have a moderate positive correlation.

FIG. 11 is a plot of the droplet encapsulation efficiency as a function of a parameter that is given by the equation $$\frac{(RealConcentration) \times (FinalDropletDiameter)^3}{(DropletFormationFrequency)^{1/2}} (\times 10^{-2} s^{1/2}).$$

It is observed from FIG. 11 that the droplet encapsulation efficiency increases as the droplet diameter increases and/or the droplet formation frequency decreases. It is noted that the size of the cells trapped can depend on the geometry (e.g. diameter) of the droplets generated.

As noted above, there is a positive correlation between real concentration (RC) and encapsulation efficiency (EE). Also, final droplet diameter (FDD) shows the volume of the dispersed phase in one droplet. So $FDD^3$, which is a volume term, should be considered. Lastly, there is a negative correlation between droplet formation frequency (DFF) and encapsulation efficiency because of new coming dispersed phase with initial concentration of particles. The power ½ is added to DFF in the above equation to provide a higher correlation to encapsulation efficiency (EE).

Consequently, in order to enhance the encapsulation efficiency (EE), it may be advantageous to increase real concentration (RC) and final droplet diameter (FDD) and decrease droplet formation frequency (DFF).

However, the real concentration (RC) may have a maximum limit. When RC is higher, trapped particles or cells may influence the flow field in the droplet generation region such that droplet formation may become unstable. The regime may change from dripping to geometry-controlled regime, which may release trapped particles without trapping them.

When the final droplet diameter (FDD) is increased, $d_{gap}$ may also increase. It is more likely to encapsulate two or more particles into one droplet under such conditions. When the droplet formation frequency (DFF) is decreased, the velocity at the interface V may also decrease which may reduce the capillary number Ca which can change the droplet formation region to be geometry-controlled.

Thus, in order to improve the encapsulation efficiency (EE), it may be advantageous to maintain real concentration (RC) and final droplet diameter (FDD) near their maximum limits and find materials for the continuous and dispersed phases that have appropriate viscosity of the continuous phase μ and equilibrium surface tension between the continuous and dispersed phases $\gamma_{EQ}$ to perform dripping regime under relatively low velocity V.

Various embodiments of the microfluidic device 500 can include two outlets. A microswitch may be configured to direct droplets encapsulating particles to the target outlet and direct other empty droplets to the waste outlet. Such a device may also include a sorting section that sorts droplets with and without particles prior to the section including the microswitch.

A hydrodynamic method for high-throughput encapsulation of single particles with relatively high encapsulation efficiency in drop-based microfluidic devices are discussed herein.

Although certain preferred embodiments and examples are discussed herein, it will be understood by those skilled in the art that the innovative aspects extend beyond the specifically disclosed embodiments to other alternative embodiments and/or uses of the innovative aspects and obvious modifications and equivalents thereof. In addition, while several variations of the innovative aspects have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the innovative aspects discussed herein should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method of encapsulating a solid sample in a droplet, the method comprising:
flowing a continuous phase through a first fluid channel at a first flow rate;
flowing a dispersed phase through a second fluid channel at a second flow rate, the dispersed phase comprising a plurality of particles, cells or beads;
trapping the plurality of particles, cells or beads in a mixing region that receives the dispersed phase and the continuous phase, wherein the dispersed phase flowing through the second fluid channel and the continuous phase flowing through the first fluid channel merge at the mixing region;
encapsulating the trapped plurality of particles, cells or beads in droplets of the dispersed phase in the continuous phase by using a pump to control the first flow rate of the continuous phase or the second flow rate of the dispersed phase, or by using a pressure regulator to control a pressure of the continuous phase or a pressure of the dispersed phase to generate a vortex in a flow field of the dispersed phase in the mixing region, wherein a distance (dgap) between an outermost streamline of the vortex formed in the flow field of the dispersed phase and an interface between the dispersed phase and the continuous phase is greater than or equal to a size of the particles or cells; and
exiting the droplets of the dispersed phase containing the trapped plurality of particles, cells or beads in the continuous phase from the mixing region through an orifice.

2. The method of claim 1, comprising controlling the flow rate of the continuous phase or the dispersed phase with the pump or controlling the pressure of the continuous phase or the dispersed phase with the pressure regulator, such that a distance ($d_{gap}$) between an outermost streamline of the vortex generated in flow field of the dispersed phase and an interface between the dispersed phase and the continuous phase is greater than or equal to a size of the plurality of particles, cells or beads.

3. The method of claim 1, wherein the continuous phase comprises a lipid.

4. The method of claim 1, wherein the dispersed phase comprises an aqueous material.

5. The method of claim 1, wherein the diameter of the plurality of particles, cells or beads is about 2.5 μm.

6. The method of claim 1, comprising adjusting a flow parameter of a buffer solution through a third fluid channel in communication with the mixing region to wash away particles, cells or beads having a size smaller than a predetermined size from the plurality of particles, cells or beads, wherein the adjusted flow parameter of the buffer solution through the third channel untraps particles from the mixing region having a size smaller than a desired size from the plurality of particles.

7. The method of claim 6, wherein the flow parameter of the buffer solution that is adjusted is flow velocity.

8. The method of claim 6, wherein the flow parameter of the buffer solution that is adjusted is fluid pressure.

* * * * *